United States Patent
Pendse

(10) Patent No.: US 8,409,013 B2
(45) Date of Patent: Apr. 2, 2013

(54) INTERACTIVE ELECTRONIC GAME RESULTS AS HEALTH INDICATORS

(75) Inventor: Ajit Pendse, Durham, NC (US)

(73) Assignee: Pomdevices, LLC, Durham, NC (US)

( * ) Notice: Subject to any disclaimer, the term of this patent is extended or adjusted under 35 U.S.C. 154(b) by 78 days.

(21) Appl. No.: 13/151,528

(22) Filed: Jun. 2, 2011

(65) Prior Publication Data

US 2011/0300945 A1    Dec. 8, 2011

Related U.S. Application Data

(60) Provisional application No. 61/350,749, filed on Jun. 2, 2010.

(51) Int. Cl.
   *A63F 9/24*      (2006.01)
   *A63F 13/00*     (2006.01)
   *G06F 17/00*     (2006.01)
   *G06F 19/00*     (2011.01)

(52) U.S. Cl. .......................................... 463/42; 463/43

(58) Field of Classification Search ..................... 463/42
   See application file for complete search history.

(56) References Cited

U.S. PATENT DOCUMENTS

| | | | |
|---|---|---|---|
| 4,956,825 A | 9/1990 | Wilts et al. | |
| 5,568,487 A | 10/1996 | Sitbon et al. | |
| 5,967,975 A | 10/1999 | Ridgeway | |
| 6,078,924 A | 6/2000 | Ainsbury et al. | |
| 7,111,044 B2 | 9/2006 | Lee | |
| 7,231,262 B2 | 6/2007 | Hollis et al. | |
| 7,367,888 B1 * | 5/2008 | Chen et al. | 463/42 |
| 7,586,418 B2 | 9/2009 | Cuddihy et al. | |
| 7,616,110 B2 | 11/2009 | Crump et al. | |
| 2001/0044337 A1 * | 11/2001 | Rowe et al. | 463/29 |
| 2002/0019747 A1 | 2/2002 | Ware et al. | |
| 2003/0114106 A1 | 6/2003 | Miyatsu et al. | |
| 2004/0128163 A1 | 7/2004 | Goodman et al. | |
| 2004/0203961 A1 | 10/2004 | Rustici et al. | |
| 2004/0247748 A1 | 12/2004 | Bronkema | |
| 2005/0132069 A1 | 6/2005 | Shannon et al. | |
| 2005/0151640 A1 | 7/2005 | Hastings | |
| 2006/0066448 A1 | 3/2006 | Berisford et al. | |
| 2006/0089542 A1 | 4/2006 | Sands | |

(Continued)

FOREIGN PATENT DOCUMENTS

WO    2012/027661 A1    3/2012

OTHER PUBLICATIONS

Stolowitz Ford Cowger LLP, Listing of Related Cases, Jul. 7, 2011.

(Continued)

*Primary Examiner* — Michael Cuff
*Assistant Examiner* — Kevin Y Kim
(74) *Attorney, Agent, or Firm* — Stolowitz Ford Cowger LLP

(57) ABSTRACT

In one example, a portable patient computing device receives results of a plurality of gaming sessions of a patient using a local or remote interactive electronic gaming system. The portable patient computing device identifies a trend based on the game results, or passes the game results to a caregiver computing device for remote trend identification. After the portable patient computing device receives a result of a new gaming session of the patient using a local or remote interactive gaming system, the portable patient computing device either analyzes the newly received result using the identified trend, or passes the newly received result to the remote caregiver computing device for remote analysis, or both. A caregiver of the patient is notified according to a result of the analysis.

10 Claims, 2 Drawing Sheets

U.S. PATENT DOCUMENTS

| | | | |
|---|---|---|---|
| 2006/0281543 A1* | 12/2006 | Sutton et al. | 463/29 |
| 2006/0287068 A1* | 12/2006 | Walker et al. | 463/25 |
| 2007/0066403 A1* | 3/2007 | Conkwright | 463/43 |
| 2007/0200927 A1 | 8/2007 | Krenik | |
| 2008/0027337 A1 | 1/2008 | Dugan et al. | |
| 2008/0218376 A1 | 9/2008 | Dicks et al. | |
| 2008/0243544 A1 | 10/2008 | Cafer | |
| 2009/0098925 A1* | 4/2009 | Gagner et al. | 463/20 |
| 2009/0319298 A1 | 12/2009 | Weiss et al. | |
| 2010/0023348 A1 | 1/2010 | Hardee et al. | |
| 2012/0050066 A1 | 3/2012 | Pendse | |
| 2012/0052833 A1 | 3/2012 | Pendse | |

OTHER PUBLICATIONS

United States PCT Office, "International Search Report and Written Opinion of the International Searching Authority" for PCT/US11/36093 filed on May 11, 2011; Aug. 23, 2011.

United States PCT Office, "International Search Report and Written Opinion of the International Searching Authority" for PCT/US11/38960 filed on Jun. 2, 2011; Aug. 26, 2011.

United States PCT Office, "International Search Report and Written Opinion of the International Searching Authority" for PCT/US11/49332 filed on Aug. 26, 2011; Dec. 19, 2011.

Stolowitz Ford Cowger, Listing of Related Cases, Dec. 28, 2011.

* cited by examiner

INTERACTIVE ELECTRONIC GAME RESULTS AS HEALTH INDICATORS

This application is a non-provisional of U.S. Provisional Application No. 61/350,749 filed on Jun. 2, 2010, entitled: COGNITIVE AGILITY GAME RESULTS THROUGH MOBILE TECHNOLOGIES AS HEALTH INDICATORS, which is herein incorporated by reference in its entirety.

COPYRIGHT NOTICE

© 2011 pomdevices, LLC. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

BACKGROUND OF THE INVENTION

Early detection of a decline in health, especially cognitive health, in an older adult can be critical for effective treatment. Checkups at medical facilities can be useful for early detection, but are sometimes too infrequent to provide immediate detection of a decline in health, especially cognitive health where declines can happen rapidly and without being easily noticed by friends and family.

Systems for monitoring health remotely with respect to the medical facilities, for example monitoring health in the home, do exist. Some of these existing systems fail to make adequate use of resources that may already be available in the home of the older adult, which can result in these existing systems being prohibitively expensive and/or difficult to deploy. Some of these existing systems monitor only physical health indicators, such as a heartbeat, but do not monitor cognitive health indicators, such as cognitive agility. The disclosure that follows solves these and other problems.

SUMMARY OF THE INVENTION

In one example, a portable patient computing device remote from a caregiver receives first information for a first gameplay session spanning a first time range, the first information including at least one of a numerical score resulting from the first gameplay session, an in-game achievement resulting from the first gameplay session, or play duration resulting from the first gameplay session. The portable patient computing device receives second information for a second gameplay session spanning a second time range that begins after an end of the first time range, the second information including at least one of a numerical game score resulting from a second gameplay session, a game achievement resulting from the second gameplay session, or play duration resulting from the second gameplay session.

The portable patient computing device either identifies a trend based on the collected first and second information, or passes the first and second information to a remote caregiver computing device for remote trend identification. After the portable patient computing device receives third information for a third gameplay session spanning a third time range that begins after an end of the second time range, the third information including at least one of a numerical game score resulting from the third gameplay session, a game achievement resulting from the third gameplay session, or play duration resulting from the second gameplay session, the portable patient computing device may analyze the third information using the identified trend. The portable patient computing device may pass the third information to the remote caregiver computing device for remote analysis. Either the portable patient computing device or the remote caregiver computing device (or both) notifies a caregiver according to the analysis.

In this application and the claims, we use the term "patient" broadly to mean any individual person whose activities are monitored consistent with the present disclosure. We use the term "caregiver" broadly to mean any person who receives notifications related to patient activities consistent with the present disclosure. "Caregiver" thus may include but is not limited to a doctor, nurse, other healthcare professional, friend, neighbor, family member, etc. And we use the term "home,", as in the patient's home, broadly to refer to any location where the patient spends much of their time.

DETAILED DESCRIPTION OF PREFERRED EMBODIMENTS

Figure 1:
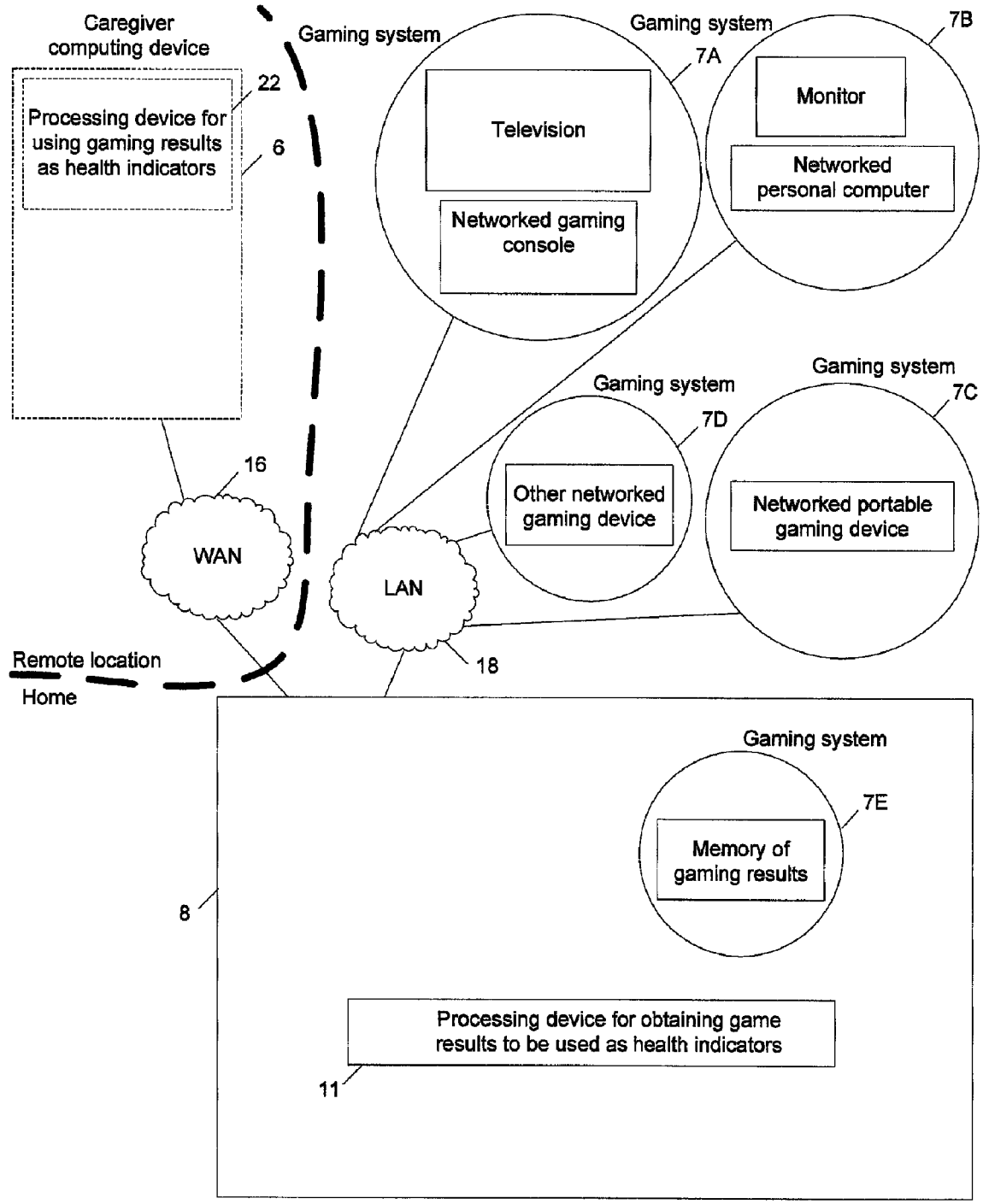
FIG. 1 illustrates a system to collect interactive game results of gaming systems in the household for identifying health changes at a remote location.

FIG. 1 illustrates a system to collect interactive game results of gaming systems in the household for identifying health changes at a remote location.

The system 100 includes a portable patient computing device 8 operated by a patient in the home and a caregiver computing device 6 operating in a remote location. The portable patient computing device 8 contains processing device 11 to obtain game results generated by in-home gameplay by the patient.

The system 100 also includes one or more of the other gaming system(s) 7A-D that are communicatively coupled to the processing device 8 over at least one network (such as LAN 18). The gaming systems 7A-D can include, but are not limited to, a networked gaming console connected to a display such as a television, a networked personal computer having a game stored thereon, a networked portable gaming device such as a cell phone having a game stored thereon, or any other gaming system. Furthermore, the system can include a gaming system 7E operated by the portable patient computing device itself, e.g. a manufacturer installed game or user downloaded game that utilizes an input/output interface of the device 8 for gameplay.

The portable computing device 8 is configured to obtain game results of in-home gameplay of at least one of the gaming systems 7A-E. In some examples, the game results from gaming systems 7A-D are collected solely over the LAN 18. In other examples, one of the gaming systems 7A-D may upload gaming results to a game server, and in those cases the portable patient computing device 8 can be configured to collect gaming results over the WAN 16 from the gaming server instead or in addition to collection over the LAN 18. Also, in other examples portable ones of the gaming systems 7A-D such as a cell phone may be played outside the home. In some cases the game results may be collected over the WAN 16 at any time, or in other cases collected over the LAN 18 when the portable gaming system 7C comes in range.

The processing device 11 can be configured to, at various times, extract information from the gaming systems 7A-E. The extracted information can include, but is not limited to, score/achievements, frequency of play, duration of play, etc. The various times for extraction could be scheduled or requested ad hoc by the caregiver computing device 6. In other embodiments, networked devices may initiate a communication, or "push" data when they have activity to report. For example, a gaming console may report a score at the conclusion of a game.

Once the processing device 11 has obtained the raw information from gaming systems 7A-E as described above, in the present example the processing device 11 processes the information to identify a trend based on the raw information from gaming systems 7A-E. It should be apparent that any known form of trend analysis can be used.

Having identified a trend, the processing device 11 can compare new information extracted from one of the devices 7A-E to the identified trend. If the new information varies from the identified trend by a predetermined threshold, the processing device 11 transmits a certain type of notification (a health alert) to a caregiver. The transmitted notification can use SMS/text messaging, email, and/or other forms of communication. If the new information does not vary from the identified trend by the predetermined threshold, the processing device 11 can still transmit a result of the trend analysis to the caregiver, although this would not be a health alert type notification. An identified trend could be based on frequency of completed gameplay sessions, and a detected variation from the trend could be represented by the lack of new gameplay results at a time expected based on the trend.

In the case of the patient playing more than one gaming system, the analysis based on the trend can also check a variance in the gameplay results from one gaming system and correlate that variance with gameplay results from other gaming systems, and based on this comparison, determine whether or not a threshold limit has been reached. For example, a person who usually plays a portable gaming device may occasionally spend more time playing a gaming console. Lack of gaming results from the portable gaming device might be compensated by the gaming results from gameplay using the gaming console (meaning no health alert is sent). Or, perhaps input from another source indicates no gameplay with any of the gaming systems, which would mean that the health alert does get sent.

The content of the uploaded notification can include results of the trend analysis to be used by the caregiver in monitoring cognitive health (or for that matter any form of health) of the patient. In some examples, the notification can be configured to highlight new deviations from existing trends and/or to characterize such new deviations by associating at least some of the trends with symptoms and characterize symptoms.

The stored trend may be located in a memory of the portable patient computing device 8. The processing device 11 may update the stored trend from time to time. An update can occur at a scheduled time no matter how much or how little new information is available, or may occur in response to receiving a certain amount of new information.

Having now described the portable patient computing device 8 and the processing device 11 in one example of the system 100, it is noted that other examples can include a caregiver computing device 6 containing processing device 22. Some or all of the functions described above by the processing device 11 can be performed by the processing device 22 as part of a distributed scheme.

For example, in one distributed scheme, the processing device 11 can upload the raw information extracted from the gaming systems 7A-E via SMS/text messaging, email, and/or other forms of communication. Periodically or upon request, the processing device 22 determines a trend based on all of the raw information currently available on the computing device 6. The processing device 22 stores the determined trend data on a local memory or a network accessible remote memory. Then, as the portable patient computing device 8 feeds new raw information to the computing device 6, the processing device 22 can compare the new raw information to the stored trend data. According to the comparison, the processing device 22 can notify a caregiver, which may include displaying a message on a display attached to the computing device 6.

It should be apparent that the above example is just one example of distributing functions between the processing device 11 and the processing device 22. In other examples the functions can be distributed in any combination.

The present disclosure includes daily (or other period) gameplay monitoring. The system then builds a database of information over time. The database can then be analyzed for trends and deviations from those trends, and the results could be communicated to appropriate parties such as caregivers or medical facilities. The database can be located on a portable patient computing device or on a network device remote from the portable patient computing device, or even distributed across multiple network devices including the portable patient computing device.

Trends can be determined through a moving average algorithm such that both acute and longitudinal changes can be detected. Some specific embodiments would not only provide status and alerts, but could include recommended actions for both the caregiver and the patient.

Figure 2:
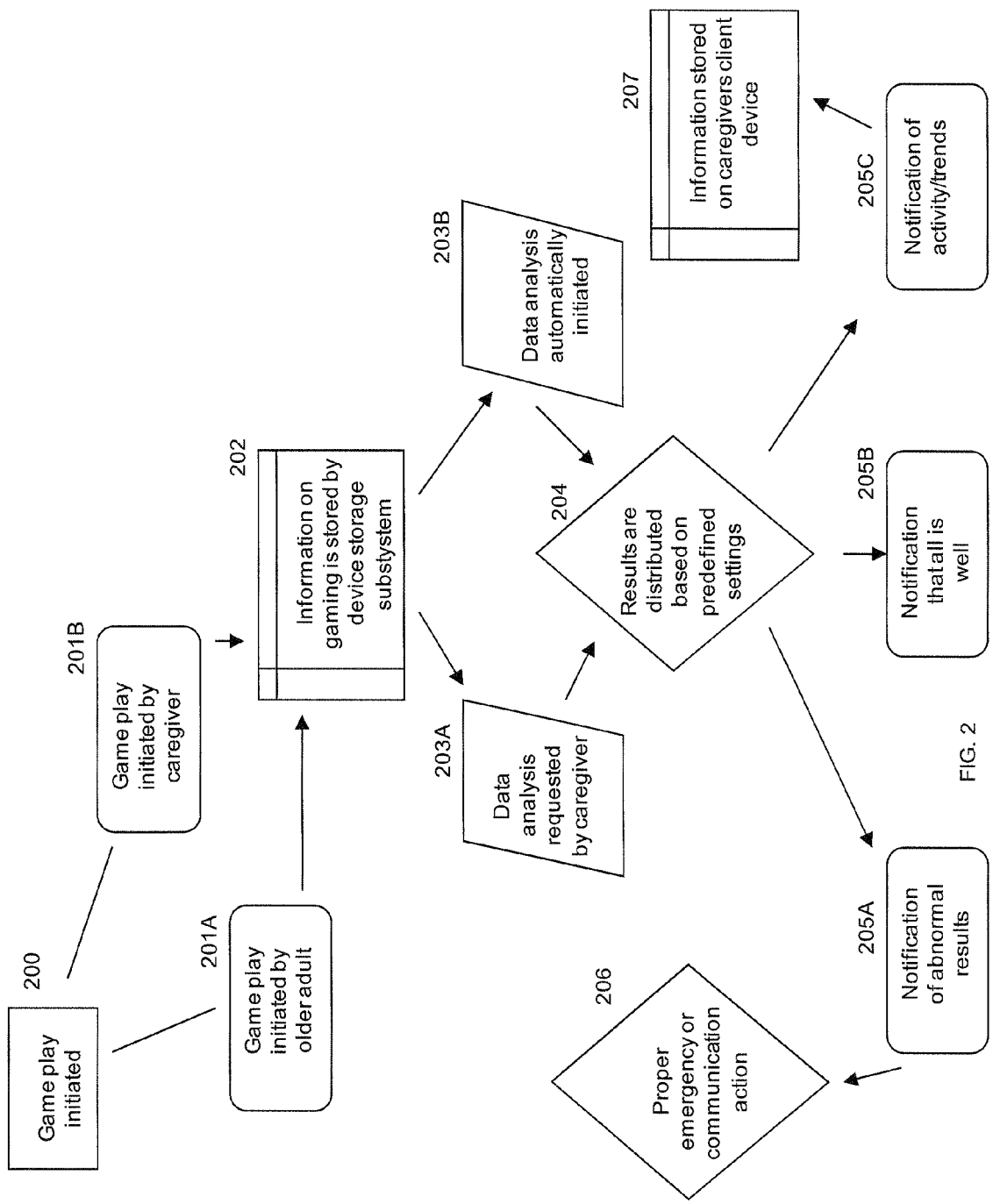
FIG. 2 illustrates an example method for using the caregiver computing device and/or the patient computing device shown in FIG. 1.

FIG. 2 illustrates an example method for using the caregiver computing device and/or the patient computing device shown in FIG. 1.

In process 200 a game session is initiated by a patient, either at the preference of the patient (201A) or the caregiver (201B). Gameplay can be on any interactive electronic device, such as the computing device 8 or a remote interactive electronic device. In process 202 information from the gaming session is stored in the computing device 8 or the networked gaming system.

In process 203A or 203B, analysis of the stored information is requested. The analysis can be requested by the device 6 at any time or automatically initiated as part of a preset schedule. The analysis typically includes comparison of the information from a most recent gaming session to information from at least one previous session.

The stored information can then be analyzed, for example by the computing device 8, for trends and deviations from those trends. Trends can be determined through a moving average algorithm such that both acute and longitudinal changes can be detected. Some specific embodiments would identify trends and deviations therefrom in the analysis, but could also identify recommended actions for both the caregiver and the patient.

In process 204 results of the analysis are distributed based on predefined settings. For example, the results of the analysis can be sent to a stored list of recipients. The device 6 may be included as a recipient.

Along with sending the results, the device 8 can also include a notification 205A-B based on any identified recommend actions resulting from the analysis. In the case of an emergency 206, the notification can be sent differently (for example by phone call instead of email) and/or be sent to a relevant emergency response group. The device 8 also sends trend information in process 205C, which will be stored in a database in process 207 once received by the device 6.

It will be apparent to those having skill in the art that many changes may be made to the details of the above-described embodiments without departing from the underlying principles of the invention. For example, the scope of the present invention should, therefore, be determined only by the following claims.

Most of the equipment discussed above comprises hardware and associated software. For example, the typical portable device is likely to include one or more processors and software executable on those processors to carry out the operations described. We use the term software herein in its commonly understood sense to refer to programs or routines (subroutines, objects, plug-ins, etc.), as well as data, usable by a machine or processor. As is well known, computer programs generally comprise instructions that are stored in machine-readable or computer-readable storage media. Some embodiments of the present invention may include executable programs or instructions that are stored in machine-readable or computer-readable storage media, such as a digital memory. We do not imply that a "computer" in the conventional sense is required in any particular embodiment. For example, various processors, embedded or otherwise, may be used in equipment such as the components described herein.

Memory for storing software again is well known. In some embodiments, memory associated with a given processor may be stored in the same physical device as the processor ("on-board" memory); for example, RAM or FLASH memory disposed within an integrated circuit microprocessor or the like. In other examples, the memory comprises an independent device, such as an external disk drive, storage array, or portable FLASH key fob. In such cases, the memory becomes "associated" with the digital processor when the two are operatively coupled together, or in communication with each other, for example by an I/O port, network connection, etc. such that the processor can read a file stored on the memory. Associated memory may be "read only" by design (ROM) or by virtue of permission settings, or not. Other examples include but are not limited to WORM, EPROM, EEPROM, FLASH, etc. Those technologies often are implemented in solid state semiconductor devices. Other memories may comprise moving parts, such as a conventional rotating disk drive. All such memories are "machine readable" or "computer-readable" and may be used to store executable instructions for implementing the functions described herein.

A "software product" refers to a memory device in which a series of executable instructions are stored in a machine-readable form so that a suitable machine or processor, with appropriate access to the software product, can execute the instructions to carry out a process implemented by the instructions. Software products are sometimes used to distribute software. Any type of machine-readable memory, including without limitation those summarized above, may be used to make a software product. That said, it is also known that software can be distributed via electronic transmission ("download"), in which case there typically will be a corresponding software product at the transmitting end of the transmission, or the receiving end, or both.

Having described and illustrated the principles of the invention in a preferred embodiment thereof, it should be apparent that the invention may be modified in arrangement and detail without departing from such principles. We claim all modifications and variations coming within the spirit and scope of the following claims.

The invention claimed is:

1. A system, comprising:
   a portable device including a processing device and a network interface to communicate over a network, the processing device configured to:
   collect over the network first information at a first time, the first information including at least one of a numerical score resulting from a first gameplay session using an interactive electronic gaming device, an in-game achievement resulting from the first gameplay session, or play duration resulting from the first gameplay session;
   collect over the network second information at a second different time, the second information including at least one of a numerical game score resulting from a second gameplay session using the interactive electronic gaming device, a game achievement resulting from the second gameplay session, or play duration resulting from the second gameplay session;
   identify a moving average based on the collected first and second information;
   collect over the network third information at a third different time, the third information including at least one of a numerical game score resulting from a third gameplay session using the interactive electronic gaming device, a game achievement resulting from the third gameplay session, or play duration resulting from the third gameplay session;
   compare the third information to the identified moving average; and
   notify a caregiver responsive to the comparison.

2. The system of claim 1, wherein the processing device is configured to:
   determine a difference between the third information and the identified moving average; and
   transmit a message if the difference exceeds a preset threshold.

3. A method, comprising:
   providing first information including at least one of a numerical score of a first gameplay session, an in-game achievement of the first gameplay session, or play duration of the first gameplay session;
   wherein the first gameplay session spans a first time range;
   providing second information including at least one of a numerical game score of a second gameplay session, a game achievement of the second gameplay session, or play duration of the second gameplay session;
   wherein the second gameplay session spans a second time range that begins after an end of the first time range;
   identifying, using an electronic device, a moving average based on the provided first and second information;
   providing third information including at least one of a numerical game score of a third gameplay session, a game achievement of the third gameplay session, or play duration of the third gameplay session;
   wherein the third gameplay session spans a third time range that begins after an end of the second time range;
   comparing using the electronic device the third information to the identified moving average; and
   notifying using the electronic device a caregiver responsive to the comparison, the notifying including at least one selected from the group comprising transmitting over an electronic network a notification responsive to the comparison and outputting to a local display device the notification responsive to the comparison.

4. The method of claim 3,
   wherein the first, second, and third gameplay sessions result from operation of a game operating on a portable patient computing device.

5. The method of claim 3, wherein the first, second, and third gameplay sessions result from operation of a gaming platform installed at a patient's home or other location remote from a caregiver facility.

6. The method of claim 5, wherein the gaming platform is a gaming console.

7. The method of claim 3, wherein the first, second, and third gameplay sessions result from operation of a game stored on a portable gaming platform.

8. An apparatus, comprising:
a processing device configured to:
receive first information including at least one of a numerical score resulting from a first gameplay session using an interactive electronic gaming device, an in-game achievement resulting from the first gameplay session, or play duration resulting from the first gameplay session;
wherein the first gameplay session spans a first time range;
receive second information including at least one of a numerical game score resulting from a second gameplay session using the interactive electronic gaming device, a game achievement resulting from the second gameplay session, or play duration resulting from the second gameplay session;
wherein the second gameplay session spans a second time range that begins after an end of the first time range;
identify a moving average based on the collected first and second information;
receive third information including at least one of a numerical game score resulting from a third gameplay session using the interactive electronic gaming device, a game achievement resulting from the third gameplay session, or play duration resulting from the third gameplay session;
wherein the third gameplay session spans a third time range that begins after an end of the second time range;
compare the third information to the identified moving average; and
notify a caregiver responsive to the comparison.

9. The apparatus of claim 8, further comprising:
a network interface coupled to the processing device, wherein the first, second, and third information are received over the network interface.

10. The apparatus of claim 8, wherein the processing device is further configured to:
download a game;
wherein the first, second, and third gameplay sessions result from operation of the downloaded game.

* * * * *